United States Patent [19]

Gammill

[11] 4,438,274
[45] Mar. 20, 1984

[54] ANTIATHEROSCLEROTIC FUROCHROMONES

[75] Inventor: Ronald B. Gammill, Portage, Mich.

[73] Assignee: The Upjohn Company, Kalamazoo, Mich.

[21] Appl. No.: 378,700

[22] Filed: May 17, 1982

[51] Int. Cl.$^3$ .................................... C07D 311/78
[52] U.S. Cl. .................................... 549/387; 424/283
[58] Field of Search .................................... 549/387

[56] References Cited

U.S. PATENT DOCUMENTS 2,680,119  6/1954  Robertson et al. ................ 549/387
4,284,569  8/1981  Gammill ............................ 549/387

OTHER PUBLICATIONS

Abu-Shady, H., Experiments with Khellin VII., UAR J. Pharm. Sci., 11:283-288 (1970).
Abu-Shady, H., et al., Experiments with Khellin-VIII. J. Pharm. Belg., 33:397-399 (1978).
Anrep, G. V., et al., Therapeutic Uses of Khellin, The Lancet, pp. 557-558 Apr. 26, 1947.
Anrep, G. V., et al., The Coronary Vasodilator Action of Khellin, Amer. Heart J., 37:531-542 (1949).
Apffel, C. A., Die Zytostatische Wirkung von Chinonen und Ihren Derivaten, Deut. Med. Wochschr., 80:414-416 (1955).
Aubertin, E., La Khelline, agent de relachement de la musculature lisse. J. Med. Bordeaux, 127:821-823 (1950).
Baytop, O. T., Khellin'in Yer Solucanlarina Tesiri Hakkinda, Folia Pharm. (Turkey), 1:48-49 (1949).
Best, M. M., et al., Effects of dioxyline Phosphate and Enteric-Coated Khellin on Coronary Artery Insufficiency, Amer. J. Med. Sci. 222:35-39 (1951).
Chen, G., et al., The Central Nervous Depressive Effect of Khellin, Proc. Soc. Expetl. Biol. Med., 78:305-307 (1951).
Colombo, G., et al., Sulla attivita di alcune sostanze del gruppo della Kellina sulla motilita ureterale—in vitro—, Arch. Sci. Med. 97:71-81 (1954).
Day, C. E., et al., Utility of a Selected Line (SEA) of the Japanese Quail for the Discovery of New Anti-Atherosclerosis Drugs, Laboratory Animal Science, 27:817-821 (1977).
Easton, R. P., High Density Lipoprotein—Key to Anti--Atherogenesis, J. Chron. Dis., 31:131-135 (1978).
Haust, M. D., Reaction Patterns Of Intimal Mesenchyme to Injury, and Repair in Atherosclerosis, Adv. Exp. Med. Biol., 43:35-57 (1974).
Huttrer, C. P., et al., The Chemistry and Physiological Action of Khellin and Related Products, Chem. Revs., 48:543-579 (1951).
Jordan, H., Cardiovasculare Wirkungen Intravenoser Khellin-Injektionen, Arzneimittel-Forsch 8:141-143 (1958).
Jordan, H., Cardiovasculare Wirkungen Intravenoser Khellin-Injektionen, Arzneimittel-Forsch, 7:82-85 (1957).
LaBarre, J., et al., Action protectrice de la khelline vis-a-vis de pulcere gastrique experimental provoque, chez le chien, par l'administration de cinchophene, Compt. Rend. Soc. Biol., 150:598-599 (1956).
LaBarre, J., et al., A propos de l'action inhibitrice de la khelline dans l'ulcere gastrique experimental provoque par administration journaliere de phenylbutazone, Compt. Rend. Soc. Biol., 150:1806-1807 (1956).
Lian, C., et al., Etude Experimentale et Clinique de la Khelline, Acta. Cardiol. (Brussels), 5:373-388 (1950).
Montorsi, W., et al., Sur L'Activite de Certaines Substances du Groupe de la Khelline, Presse Med., 63:81 1955).
Musante, C., et al., Furil E. Isossazol-Furo-Cromoni e Derivati, Pharmaco: (Pavie) Ed. Sci., 15:81-94 (1960).
Mustafa, A., et al., Experiments with Furochrmones, Synthesis of Ammiol and Khellol, J. Org., Chem., 26:886-890 (1961).
Mustafa, A., Furopyrans and Furopyrones, John Wiley and Sons, Inc., NY (1967) pp. 102-159 (Chapter III: Furochromones).
Osher, H. L., et al., Khellin in the Treatment of Angina Pectoris, New England J. Med., 244:315-321 (1951).
Raymond-Hamet, M., Compt. Rend., 238:1624-1626 (1954).
Samaan, K., et al., The Response of the Heart to Visammin and to Khellinin, J. Pharm. Pharmacol., 1:538-544 (1949).
Samaan, K., et al., The Existence in Ammi Visnaga of a Cardiac Depressant Principle Visammin and a Cardiac Stimulant Glycoside Khellinin, J. Roy, Egypt Med. Assoc., 33:953-960 (1950).
Schonberg, A., et al., Khellin and Allied Compounds, JACS 72:1611-1617 (1950).
Schonberg, et al., Furo-Chromones and -Coumarins. XIV. JACS 77:5439-5440 (1955).
Schurr, P. E., High Volume Screening Procedure for Hypobetalipoproteinemia Activity in Rats, Adv. Exp. Med. Biol. 67: Atherosclerotic Drug Discovery, pp. 215-229, Plenum Press (1975).
Silber, E. N., The Effect of Khellin on Cardio-Pulmonary Function in Chronic Pulmonary Disease, published in 1951.
Swayne, V. R., et al., Spermicidal Action of Khellin, Amer. J. Pharm., 125:295-298 (1953).

Primary Examiner—Nicky Chan
Attorney, Agent, or Firm—Lawrence T. Welch; Robert A. Armitage

[57] ABSTRACT

The present specification provides novel analogs of khellin, a natural product, which are useful in the treatment and prevention of atherosclerosis. Particularly, the present disclosure provides novel 5H-furo[3,2-g]-benzopyran-5-one substituted at the four and nine positions by methoxy or optionally substituted at the four position by hydroxy or alkoxy groups other than methoxy, certain 7-(N,N-dialkylaminoethen-2-yl substituted compounds. Also provided are certain novel antiatherosclerotic 7H-furo[3,2-g][1]benzopyrans.

4 Claims, No Drawings

ANTIATHEROSCLEROTIC FUROCHROMONES

DESCRIPTION

Background of the Invention

The present specification provides novel compositions of matter and novel methods of their preparation.

The present specification particularly relates to novel analogs of a known pharmacological agent, khellin, also known as "visamin", and structurally related antiatherogenic furochromones and other benzopyrans. Chemically, khellin is a furochromone. Furochromones are characterized generally by the structural formula IV. Specifically, khellin is the furochromone of formula V, and is trivially named 7-methyl-4,9-dimethoxyfurochromone. Khellin and related furochromones are naturally-occurring substances and have been used in crude form as pharmacological agents for centuries. Khellin is an extract from the plant Ammi visnaga. This plant grows wild in Eastern Mediterranean countries. Aside from khellin, Ammi visnaga is also a source of at least three other known and characterized furochromones, specifically visnagin, khellinin, and ammiol.

As indicated above, khellin exhibits a wide variety of pharmacological actions, rendering this compound a useful agent for numerous pharmacological purposes. For a comprehensive, but somewhat dated, review of the chemistry and physiological action of khellin-related products, see the reports of Huttrer, C. P., et al., Chem. Revs. 48:543-79 (1951) and Aubertin, E., J. Med. Bordeaux 127:821-823 (1950).

One principal action of khellin is its ability to induce relaxation of smooth muscle tissues. Particularly, khellin is known as a potent dilator of coronary blood vessels. This potent coronary vasodilator activity of khellin renders the compound useful in the treatment of angina pectoris and other diseases characterized by coronary artery insufficiency. For a description of the use of khellin in the treatment of such diseases, see Osher, H. L., et al., "Khellin in the Treatment of Angina Pectoris", The New England Journal of Medicine 244:315 (1951). Also the effects of enteric-coated khellin on coronary artery insufficiency is reported by Best, M. M., et al., J. Med. Sci. 222:35-9 (1951). The ability of khellin to relax smooth muscle also extends to gastrointestinal smooth muscle where khellin has been demonstrated to inhibit peristalsis, thus indicating antidiarrhetic potential. See Raymond-Hamet, M., Compt. Rend. 238:1624-6 (1954). Khellin may also be useful for the treatment of gastrointestinal disorders exhibiting a spasmotic component, as suggested by Anrep, G. V., et al., Amer. Heart J. 37:531-542 (1949). Further the antispasmotic effects of khellin on the urethra is reported by Colombo, G., et al., Arch. Sci. Med. 97:71 (1954) and Mantorsi, W., et al., Presse Med. 63:81 (1955).

The antispasmotic action of khellin also extends to bronchial smooth muscle, rendering khellin useful in the treatment of asthma and other hypoxic pulmonary diseases. In this regard, see Silber, E. N., et al., "The Effect of Khellin on Cardio-Pulmonary Function in Chronic Pulmonary Disease", published in 1951; Anrep, G. V., et al., "Therapeutic Uses of Khellin", The Lancet, April 26, 1947, pages 557-8.

Khellin has also been reported to exert a hypotensive effect in humans by Jordan, H., Arzneimittel-Forsch 8:141-3 (1958), and 7:82-5 (1957). An additional account of the hypotensive effect of khellin is provided by Lian, C., et al., Acta. Cardiol. (Brussels) 5:373-88 (1950). With respect to overall cardiac effects, however, khellin has been reported to exert a cardiac depressive activity. In this regard see Samaan, K., et al., J. Roy. Egypt Med. Assoc. 33:953 (1950) and J. Pharm. Pharmacol. 1:538-44 (1949).

In addition to its effect on gastrointestinal smooth muscle reported above, khellin is also known as a gastric antisecretory and antiulcer agent. In this regard, the gastric antisecretory activity of khellin is reported by LaBarre, J., Compt. Rend. Soc. Biol. 150:1806-7 (1956) and 150:598-9 (1956).

Numerous other miscellaneous properties of khellin are also reported. For an account of its anthelminic activity see Baytop, O. T., Folia, Pharm. (Turkey) 1:48-9 (1949). For an account of the CNS depressant activity of khellin see Chen, G., Proc. Soc. Expetl. Biol. Med. 78:305-7 (1951). For an account of the cytostatic activity of khellin see Apffel, C. A., Deut. Med. Wochschr. 80:414-16 (1955). Finally, the spermacidal action of khellin is reported by Swayne, V. R., et al., Amer. J. Pharm. 125:295-8 (1953).

Khellin and numerous chemically related furochromones (and derivatives thereof) are also useful in treatment and prevention of atherosclerosis by methods described in U.S. Pat. No. 4,284,569.

Atherosclerosis in mammals is a disease characterized by the deposition of atherosclerotic plaque on arterial walls. While atherosclerosis exhibits many varied forms and consequences, typical consequences of atherosclerotic diseases include angine pectoris, myocardial infarction, stroke and transient cerebral ischemic attacks. Other forms of atherosclerotic diseases include certain peripheral vascular diseases and other ischemias (e.g., bowel and renal).

Medical science now recognizes that certain forms of athero sclerosis may be preventable or reversible. Agents capable of preventing or reversing atherosclerosis are characterized as exhibiting antiatherosclerotic activity. Since serum lipids have a recognized association with atherogenesis, an important class of antiatherosclerotic agents are those with serum lipid-modifying effects. Serum lipids implicated in atherogenesis include serum cholesterol, serum triglycerides, and serum lipoproteins.

With respect to serum lipoproteins, at least three different classes of these substances have been characterized: high density lipoproteins (HDL's), low density lipoproteins (LDL's), and very low density lipoproteins (VLDL's). HDL's are often referred to as alphalipoproteins, while LDL's and VLDL's are referred to as betalipoproteins. The enhancement to HDL levels (hyperalpha-lipoproteinemic activity) is postulated to have direct antiatherosclerotic effects. See Eaton, R. P., J. Chron. Dis. 31:131-135 (1978). In contrast, agents which reduce serum LDL's and serum VLDL's (hypobetalipoproteinemic agents) are also associated with antiatherogenic effects. See Haust, M. D., "Reaction Patterns of Intimal Mesenchyme to Injury and Repair in Atherosclerosis:," Adv. Exp. Med. Biol. 43:35-57 (1974), which postulates that serum LDL is a factor in atherosclerotic lesion formation.

Numerous animal models have been developed for assessing antiatherogenic activity. Principal among these are models for assessing hypobetalipoproteinemic activity in the rat, antiatherosclerotic activity in the Japanese quail, and lipoprotein modifying activity in the monkey. For a description of the operation of the hypobetalipoproteinemic rat model, refer to the known methods of Schurr, P. E., et al., "High Volume Screening Procedure for Hypobetalipoproteinemia Activity in Rats", Adv. Exp. Med. Biol. 67: Atherosclerotic Drug Discovery, pp. 215-229, Plenum Press (1975). For a description of the Japanese quail model, see Day, C. E., et al., "Utility of a Selected Line (SEA) of the Japanese Quail (Coturnic Coturnix japonica) for the Discovery of New Anti-Atherosclerosis Drugs", Laboratory Animal Science 27:817-821 (1977).

A suitable primate model for assessing antiatherosclerotic activity of chemical compounds is found in the cynomolgus monkey. In these animals base-line values for VLDL's, LDL's, and HDL's can be determined by controlling diet over a period of several weeks and sampling plasma daily. After establishing control values, the effects of drug treatment are assessed by administering by gavage with a predetermined series of doses of test compounds for a similar period (e.g., two weeks).

The khellin, the khellin-related products of Ammi visnaga, and related furochromones (and derivatives) described in U.S. Pat. No. 4,284,569 are all characterized by pronounced antiatherogenic activity, rendering these compounds useful in the treatment and prophylaxis of atheroscherosis, atherogenic hyperlipoproteinemia (i.e., hypobetalipoproteinemia) and atherogenic hypolipoproteinemia (i.e., hypoalphalipoproteinemia), and the untoward consequences thereof. These compounds exhibit this useful pharmacological activity in both mammalian and non-mammalian species, including humans.

The patients susceptible to the development of atherosclerotic diseases and the untoward consequences thereof are particularly those physically asymptomatic patients manifesting one or more risk factors known to predispose one to disease development. Such risk factors are high serum cholesterol and serum triglycerides, hypertension, obesity, diabetes, and genetic predisposition. Patients manifesting two or more risk factors are deemed to be especially susceptible to atherosclerotic diseases. These khellin-related materials all exhibit pronounced oral pharmacologic activity. Accordingly, in using these compounds for the treatment of atherosclerosis, an oral route of administration, either by conventional oral dosage forms or by mixture with food, represents the preferred method of their systemic administration. Alternatively, however, these compounds may be administered by other convenient routes of administration whereby systemic activity is obtained. These other routes of administration would, accordingly, include rectal, vaginal, subcutaneous, intravenous, and like routes.

In humans, the preferred route of administration is oral, in the form of capsules or tablets containing the drug.

The patient or animal being treated must be given periodic doses of the drug in amounts effective to reduce atherogenic serum lipoproteins (e.g., betalipoproteins) or selectively enhance levels of antiatherogenic serum lipoproteins (e.g., enhancing alphalipoprotein levels, while suppressing, or at least unaffecting, betalipoprotein levels). Such effective dosages are readily determined by methods known in the art. For example, small daily doses of the drug (e.g., 50-100 mg) may be administered initially with higher succeeding doses until levels of atherogenic or antiatherogenic serum lipoproteins are favorably affected. By this regimen, a compound is administered initially at doses as low as about 50 mg per patient per day, with increasing doses up to about 200 mg per patient per day. In the event the antiatherogenic response in a patient being treated at a dose of 200 mg per day is insufficient, higher doses are also utilized to the extent patient tolerance permits further increases in dose.

While the preferred dosage regimen is with single daily dosing of patients, also preferred for obtaining more uniform serum levels of drug are multiple dosages per day (e.g. up to 4-6 times daily). Accordingly, when 4 daily doses of drug are to be administered, each such dose may be about 50 mg per patient per dose (200-300 mg per patient per dose), or higher depending on tolerance.

Similar doses are employed in non-human mammals, e.g., 1-5 mg/kg/day.

4,9-Dimethoxyfurochromones are known in the art. Such known compounds include 7-ethyl, 7-phenyl, 7-propyl, and 7-ethoxycarbonyl analogs described by Schonberg, A., et al., JACS 72:1611-17 (1950); 7-γ-pyridyl analogs, described by Schonberg, A., JACS 77:5439 (1955); 7-furanyl analogs, described by Musante, C., et al., Pharmaco. (Pavie) Ed. Sci. 15:81-94 (1960); 7-carboxyaldehyde analogs, described by Mustafa, A., et al., J. Org. Chem. 26:886 (1961). Also, 6-substituted-4,9-dimethoxyfurochromones are known. See, for example, the compounds described by Abu-Shady, H., UAR J. Pharm. Sci. 11:283 (1970).

4-Methoxy-7-aminomethylenefurochromones are also known in the art. See Abu-Shady, H., et al, J. Pharm. Belg. 33:397 (1978).

A wide variety of antiatherosclerotic furochromones are described in U.S. Pat. No. 4,284,569.

PRIOR ART

Extensive pharmacological uses for khellin and related substances are known, as indicated above. Khellin analogs are also known in the art, as indicated above. See especially U.S. Pat. No. 4,284,569 and the review by Mustafa, A., "Furopyrans and Furopyrones," John Wiley and Sons, Inc., N.Y., N.Y. (1967), pp. 102-159 (Chapter III: Furochromones). Also see U.S. Pat. No. 2,680,119 describing 6- and/or 7-substituted furochromones, i.e., alkyl, alkoxyalkyl and phenylalkyl substituted compounds.

SUMMARY OF THE INVENTION

The present invention particularly provides:
(a) A furochromone of formula I:
wherein n is zero, one, or two;
wherein $R_1$ is hydrogen or $C_1$-$C_4$ alkyl;
wherein $R_2$ is $C_1$-$C_6$ alkyl; and
wherein $R_3$ is hydrogen or —O—CO—$R_4$;
wherein $R_4$ is $C_1$-$C_4$ alkyl, with the proviso that $R_3$ is hydrogen only when $R_1$ is hydroxy and $R_3$ is —O—CO—$R_4$ only when n is zero.

(b) A furochromone of formula I as described above wherein $R_2$ is methyl;

(c) A furochromone of formula I which is 4,9-dimethoxy-7-[(methylthioacetoxy)methyl]-5H-furo[3,2-g]-benzopyran-5-one;

(d) A furochromone of formula I which is 4-hydroxy-9-methoxy-7-[(methylthio)methyl]-5H-furo[3,2-g]-benzopyran-5-one;

(e) A furochromone of formula I which is 4-ethoxy-9-methoxy-7-[(methylthio)methyl]-5H-furo[3,2-g]-benzopyran-5-one;

(f) A furochromone of formula II:

wherein $R_7$ is —$CH_2$—$R_{11}$, wherein $R_{11}$ is hydrogen or $C_1$-$C_5$ thioalkyl;

wherein $R_8$ is —CH=CH—$NR_{12}R_{13}$ wherein $R_{12}$ and $R_{13}$, being the same or different, are $C_1$-$C_3$ alkyl; and wherein one of $R_5$ and $R_6$ is methoxy and the other is hydrogen or $R_5$ and $R_6$ are both methoxy;

(g) A furochromone of formula II which is (2'E)-4,9-dimethoxy-6-[(methylthio)methyl]-7-(1', N,N-dimethylamino-ether-2'-yl)-5M-furo[3,2-g]-benzopyran-5-one;

(h) A benzopyran of formula III:
wherein $R_{14}$ is:
(1) hydrogen;
(2) alkyl of one of 8 carbon atoms, inclusive;
(3) alkoxymethyl of 2 to 8 carbon atoms, inclusive;
(4) alkylthioalkyl of 2 to 8 carbon atoms, inclusive;
(5) trifluoromethyl;
(6) phenoxymethyl;
(7) phenylthiomethyl;
(8) phenoxymethyl or phenylthiomethyl substituted by chloro, fluoro, trifluoromethyl, alkyl of one to 3 carbon atoms or alkoxy of one to 8 carbon atoms; or
(9) cycloalkyl of 3 to 10 carbon atoms, inclusive;

(i) A benzopyran of formula III which is 4,9-dimethoxy-7-methyl-7H-furo[3,2-g][1]benzopyran.

The carbon atom content of various hydrocarbon containing moieties is indicated by a prefix designating the minimum and maximum number of carbon atoms in the moiety, i.e., the prefix $C_i$-$C_j$ indicates a carbon atoms content of the integer "i" to the integer "j" carbon atoms, inclusive. Thus, $C_1$-$C_3$ alkyl refers to alkyl of 1-3 carbon atoms, inclusive, or methyl, ethyl, propyl, and isopropyl.

With respect to the above, $C_1$-$C_4$ alkyl is methyl, ethyl, propyl, or butyl, including isomeric forms thereof. Similarly, $C_1$-$C_6$ alkyl is methyl, ethyl, propyl, butyl, pentyl, hexyl, and isomeric forms thereof.

By virtue of the tricyclic ring structure, the compounds in formulas I and II are designated as "5H-furo[3,2-g]benzopyran-5-ones". These compounds are substituted at two or more of the positions C-4, C-6, C-7 and C-9. For example, in formula II, $R_5$ represents the C-4 position, $R_6$ represents the C-9 position, $R_7$ represents the C-6 position, and $R_8$ represents the C-7 position. Similarly, compounds in formula III are all derivatives of "7H-furo[3,2-g][1]benzopyran" by virtue of the tricyclic ring structure. As in formulas I and II, $R_5$ and $R_6$ represent respectively substituents on the C-4 and C-9 positions, while $R_{14}$ represents a substituent on the C-7 position. Thus compounds disclosed in the present specification are all named as derivatives of the tricyclic ring structure from which they are derived. Thus, for example, while $R_1$ is methoxy, the compounds of of formulas so-described are "4,9-dimethoxy" compounds. More generally, when $R_1$ is alkyl, other than methyl, formula I compounds are designated as "4-alkoxy-9-methoxy" compounds.

The compounds in accordance with the present invention are all useful as antiatherosclerotic agents. Thus these compounds are employed by methods known in the art for the use of khellin and relate furochromones in the treatment and prevention of atherosclerosis. Accordingly, compounds of formulas I, II or III are employed in humans and in non-human mammals at doses from about 0.1-50 mg/kg/day orally. These compounds are used orally in conventional oral dosage forms, including capsules, tablets, and pharmaceutically acceptable liquids. Other routes of administration may also be employed, utilizing equivalent dosages and the appropriate conventional dosage form for the route of administration selected. Such alternatively dosage forms include rectal, vaginal, subcutaneous, intravenous, and like routes of administration.

Compounds of formulas I, II or III are also useful as food or food additives whereby the ingestion of food or feed by the mammal being treated results in an effective oral dose of the compound.

The novel compounds disclosed in the present specification are all prepared by methods described in the charts.

With respect to these charts, the substituents n, $R_1$, $R_2$, $R_4$, $R_5$, $R_6$, $R_7$, $R_{12}$, $R_{13}$, and $R_{14}$ are as defined above.

Chart A provides a method whereby the known formula XXI alkylthioalkyl substituted furochromone is transformed to novel formula XXV product. The formula XXI compound is known in the art. See U.S. Pat. No. 4,284,569. In accordance with the procedure of Chart A, this formula XXI compound is selectively demethylated at the $C_4$ position. This transformation is accomplished by treatment with anhydrous hydrobromic acid in an organic solvent (e.g., trichloromethane). The formula XXII alcohol is then alkylated to yield the formula XXIII furochromones wherein $R_1$ is alkyl of 2 to 4 carbon atoms. This methylation proceeds by conventional means, i.e., treatment of the formula XXII reactant with the alkyliodide corresponding to the 4-alkoxy compound of formula XXIII.

The formula XXIV sulfoxide (n=1) is then prepared by oxidation. For this oxidation, m-chloroperbenzoic acid is employed, although sodium periodate may also be used. One equivalent of the acid is employed per equivalent of reactant. To obtain the corresponding sulfone (n=2) two equivalents of oxidizing agent are employed per equivalent of reactant. When $R_1$ is methyl, the reactant is the formula XXI compound. When $R_1$ is hydrogen, the reactant is the formula XXII compound. When $R_1$ is other than methyl or hydrogen, the reactant is the formula XXXIII compound wherein $R_1$ is $C_2$-$C_4$ alkyl.

The formula XXIV sulfoxide (n=1) is then transformed to the formula XXV compound by treatment with the alkanoic anhydride corresponding to the alkanoate to be prepared. For example, when $R_4$ is methyl, acetic anhydride is employed as the acid anhydride. Preferably, a catalytic amount of p-toluenesulfonic acid is employed in this reaction. While reaction temperature of 30°-80° C. are useful, preferred reaction temperatures are 40°-50° C. Ordinarily, the formula XXV product is obtained within several minutes.

Chart B provides a method whereby the formula XXXI compound is aminated to yield the formula XXXII 7-(N,N-dialkylaminoethen-2-yl) compound. The formula XXXI compound is known in the art. See U.S. Pat. No. 4,284,569. This compound is transformed to the formula XXXII compound by treatment with the N,N-dialkylforamide dimethoxyacetal corresponding to the N,N-dialkylamino compound to be prepared. This reaction ordinarily proceeds to completion over the course of several hours and is advantageously conducted at elevated temperatures, i.e., greater than 100° C.

Chart C provides a method whereby the known formula XLI compound is transformed to the novel formula XLII compounds disclosed herein. Preparation of the formula XLI compound is described in U.S. Pat. No. 4,284,569. This compound is then transformed to the formula XLII compound by dehydration. This dehydration proceeds by conventional techniques, i.e., the use of a catalytic amount of p-toluenesolfonic acid.

According to the procedures described by the charts above, there are thus prepared each of the various novel antiatherosclerotic compounds in accordance with the present invention.

DESCRIPTION OF THE PREFERRED EMBODIMENTS

The operation of the present invention is more completely understood by the following examples:

EXAMPLE 1

4-Hydroxy-7-[(methylthio)methyl]-9-methoxy-5H-furo[3,2-g]benzopyran-5-one (Formula XXII: $R_2$ is methyl)

Refer to Chart A.

4,7-Dimethoxy-7-[(methylthio)methyl]-5H-furo[3,2-g]benzopyran-5-one (15 gr) is added to trichloromethane (250 ml). Anhydrous hydrobromic acid is then bubbled through the resulting mixture until a dark red color develops. The reaction is then heated to reflux for 45 min, cooled to ambient temperature, and diluted with water (200 ml). The organic layer is then separated, dried over magnesium sulphate, and concentrated under reduced pressure to yield 13.36 gr of title product, melting point 134°–135° C. Silica gel TLC $R_f$ is 0.91 in 1% methanol in ethyl acetate. IR absorptions (cm$^{-1}$) are observed at 3140, 3120, 2730, 1670, 1645, 1595, 1550, 1485, 1445, 1415, 1360, 1215, 1125, 1070, 1050, 850 and 770. NMR absorptions are observed at 7.62, 7.00, 6.15, 4.23, 3.62, and 2.25$\delta$.

EXAMPLE 2

4-Ethoxy-7-[(methylthio)methyl]-9-methoxy-5H-furo[3,2-g]benzopyran-5-one (Formula XXIII: $R_1$ is ethyl and $R_2$ is methyl)

Refer to Chart A.

The title product of Example 1 (4.0 gr) is added to acetone (100 ml), ethyl iodide (15 ml) and potassium carbonate (9 gr). The resulting mixture is then heated to reflux for 18 hr, cooled to ambient temperature, and concentrated under reduced pressure. The resulting solid is then washed with trichloromethane and separated by filtration. Concentration under reduced pressure yields a dark oil which is chromatographed on 300 gr of silica gel by high pressure liquid chromatography. Packing in elution with 10% ethyl acetate in trichloromethane yields 3.0 gr of title product, melting point 112°–114° C. Silica gel TLC $R_f$ is 0.78 in 1% methanol in ethyl acetate. IR absorptions (cm$^{-1}$) are observed at 3120, 1650, 1610, 1380, 1340, 1210, 1170, and 1065. NMR absorptions are observed at 7.62, 6.97, 6.15, 4.21, 4.20, 4.57, and 2.21$\delta$.

Following the procedure of Example 2 but employing another $C_1$–$C_4$ alkyl iodide in place of ethyl iodide, the corresponding 4-alkoxy-7-[(methylthio)methyl]-9-methoxy-5H-furo[3,2-g]benzopyran-5-one is obtained.

EXAMPLE 3

4,9-Dimethoxy-7-[(methylsulfinyl)methyl]-5H-furo[3,2-g]benzopyran-5-one (Formula XXIV: $R_1$ and $R_2$ are both methyl)

Refer to Chart A.

4,9-Dimethoxy-7-[(methylsulfinyl)methyl]-5H-furo[3,2-g]benzopyran-5-one (22.5 gr) is added to sodium methaperiodate (15.80 gr). The resulting mixture is then added with stirring to a solvent mixture consisting of water (200 ml), methanol (375 ml), ethyl acetate (150 ml), and tetrahydrofuran (125 ml). After stirring under nitrogen atmosphere for 3 days at ambient temperature, the resulting mixture is then filtered and the filter cake washed with methanol and trichloromethane (1:1, 200 ml) and ethyl acetate (300 ml). The resulting filtrate is then concentrated under reduced pressure and chromatographed on silica gel elluding with 5% methanol in trichloromethane. Pure title product (22 gr) is obtained, melting point 173°–174° C. Silica gel TLC $R_f$ is 0.34 in 10% methanol and trichloromethane. IR absorptions (cm$^{-1}$) are observed at 3140, 3120, 1650, 1620, 1550, 1480, 1380, 1365, and 1060. NMR absorptions are observed at 7.75, 7.05, 6.32, 4.20, 4.10, 4.05, and 2.88$\delta$.

Following the procedure of Example 3, but employing the title product of Example 2 in place of the starting material of Example 3, there is obtained 4-ethoxy-7-[(methylsulfinyl)methyl]-9-methoxy-5H-furo[3,2-g]benzopyran-5-one.

EXAMPLE 4

4,9-Dimethoxy-7-[(acetyloxy)(methylthio)methyl]-5H-furo[3,2-g]benzopyran-5-one (Formula XXV: $R_1$, $R_2$, and $R_4$ are all methyl)

Refer to Chart A.

The title product of Example 3 (5 gr) is added to acetic anhydride (50 ml). The resulting mixture is then warmed until homogeneity is obtained and p-toluenesulfonic acid (20 mg) is then added. The reaction temperature is then raised to 40° C. for 5 min and concentrated under reduced pressure to yield a solvent. The resultant solvent is then washed with methanol and filtered to yield pure title product (4.2 gr). Recrystallization from ethyl acetate and hexane yields crystalline material, melting point 125°–127° C. Silica gel TLC $R_f$ is 0.75 in 1% methanol and ethyl acetate. IR absorptions (cm$^{-1}$) are observed at 3120, 3080, 1750, 1660, 1635, 1610, 1555, 1480, 1355, 1210, 1135, 1090, 1070, 1020, 940, 845, and 870. NMR absorptions are observed at 7.75, 7.10, 6.78, 6.40, 4.22, 4.10, and 2.29$\delta$.

EXAMPLE 5

(2'E)-4,9-Dimethoxy-6-[(methylthio)methyl]-7-(1',N-dimethylamino-ethen-2'-yl)-5H-furo[2,3-g]benzopyran-5-one (Formula XXXI: $R_5$ and $R_6$ are both methoxy, $R_7$ is methylthiomethyl, and $R_{12}$ and $R_{13}$ are both methyl).

Refer to Chart B.

4,9-Dimethoxy-6[(methiothio)methyl]-5H-furo[2,3-g]benzopyran-5-one (6.0 gr) and N,N-dimethylformamide dimethoxy acetal (8 ml) are heated for 3 hr at 150° C. The reaction is then allowed to cool at ambient temperature and concentrated under reduced pressure to a solid. The resulting solid is then washed with diethyl ether to yield 4.58 gr of pure title product, melting point 160°–162° C. Silica gel TLC $R_f$ is 0.57 in 1% methanol and ethyl acetate. IR absorptions (cm$^{-1}$) are observed at 3140, 3120, 1630, 1620, 1600, 1575, 1545, 1380, 1345, 1270, 1135, 1095, 1065, 955, and 780. NMR absorptions are observed at 7.55, 7.51, 6.95, 5.08, 4.15, 4.03, 3.78, 3.0, and 2.15δ.

EXAMPLE 6

4,9-Dimethoxy-7-methyl-7H-furo[3,2-g][1]benzopyran (Formula XXXII: $R_5$ and $R_6$ are both methoxy, $R_{14}$ is methyl).

Refer to Chart C.

A mixture of benzene (100 ml), 6,7-dihydro-4,9-dimethoxy-7-methyl-5H-furo[3,2-g][1]benzopyran-5-ol (5.18 gr), and p-toluenesolfonic acid (5 mg) are mixed with heating to reflux for one hr, during which time 0.3 ml of water is collected from evaporation. After cooling to ambient temperature the resulting solution is treated with 20 ml of sodium bicarbonate and dried with magnesium sulphate. Concentration under reduced pressure yields a residue which is chromatographed elluding with 20% ethyl acetate in hexane. The resulting title product is obtained as a colorless liquid (4.25 gr). Silica gel TLC $R_f$ is 0.34 in 25% ethyl acetate in hexane. IR absorptions (cm$^{-1}$) are observed at 3120, 3060, 1640, 1620, 1545, 1485, 1245, 1140, 1065, and 725. NMR absorptions are observed at 7.46, 6.80, 5.70, 5.00, 4.05, 3.97, and 1.47δ.

Following the procedure of Example 6 but employing Formula XLI reactants wherein $R_{14}$ is other than methyl corresponding Formula XXII products wherein $R_{14}$ is other than methyl are obtained.

Following the examples above, there are accordingly prepared each of the various novel compounds of the present disclosure.

FORMULAS

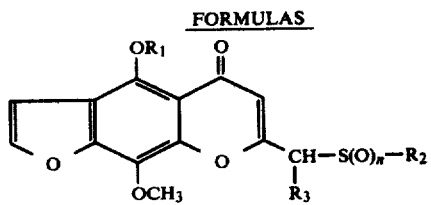
I

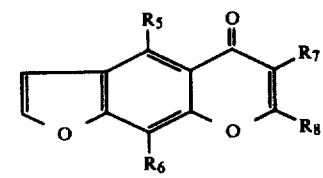
II

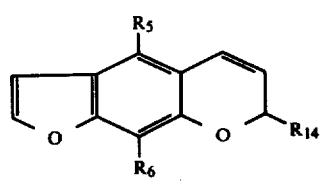
III

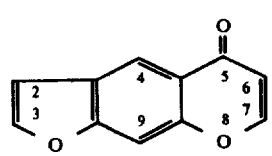
IV

-continued
FORMULAS

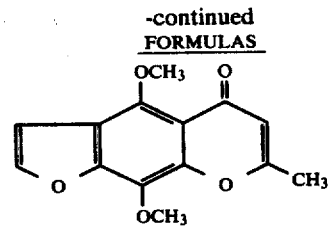
V

CHART A

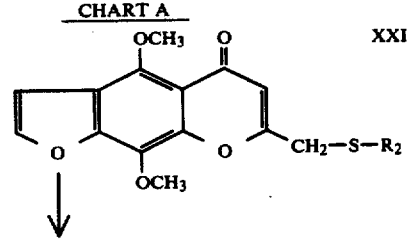
XXI

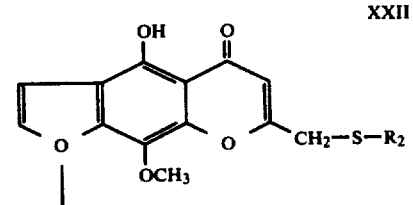
XXII

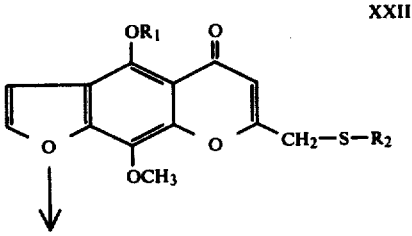
XXIII

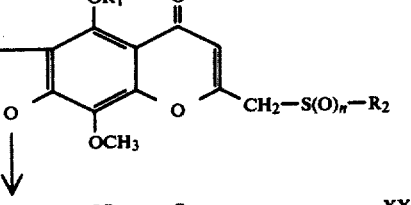
XXIV

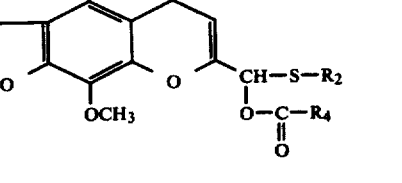
XXV

CHART B

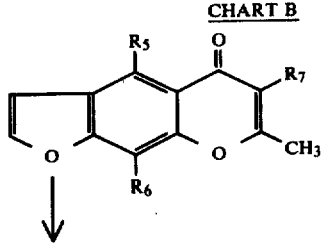
XXXI

CHART B

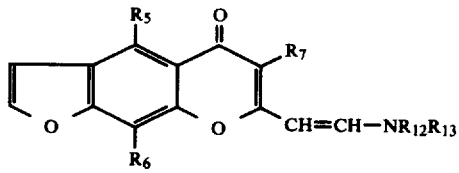

XXXII

CHART C

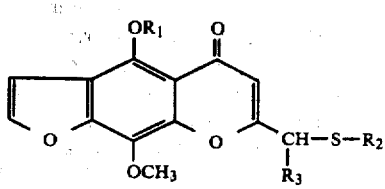

-continued
CHART C

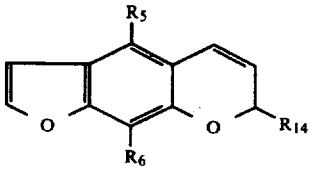

XLII

I claim:
1. A furochromone of formula I

OR₁ ... (structure shown)

wherein $R_1$ is $C_{1-4}$ alkyl;
wherein $R_2$ is $C_{1-6}$ alkyl; and
wherein $R_3$ is —O—CO—$R_4$, wherein $R_4$ is $C_1$-$C_4$ alkyl.

2. A furochromone according to claim 1 wherein $R_1$ is methyl or ethyl.

3. A furochromone according to claim 1 wherein $R_2$ is methyl.

4. 4,9-Dimethoxy-7-[(acetyloxy)(methythio)methyl]-5H-furo[3,2-g]-benzopyran-5-one, a furochrome according to claim 3.

* * * * *